US012743732B1

(12) United States Patent
Prasad et al.

(10) Patent No.: US 12,743,732 B1
(45) Date of Patent: Sep. 22, 2026

(54) SYSTEM, METHOD AND APPARATUS FOR WEARABLE COMPUTING

(71) Applicant: United Services Automobile Association, San Antonio, TX (US)

(72) Inventors: Bharat Prasad, San Antonio, TX (US); Wayne Maurice Hartman, San Antonio, TX (US); Jonathan W. Barlow, D'hanis, TX (US); Bradly J. Billman, Celina, TX (US); Charles L. Oakes, III, Boerne, TX (US); Joshua D. Maldonado, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 183 days.

(21) Appl. No.: 18/222,542

(22) Filed: Jul. 17, 2023

Related U.S. Application Data

(63) Continuation-in-part of application No. 14/941,234, filed on Nov. 13, 2015, now Pat. No. 11,868,968.

(60) Provisional application No. 62/079,649, filed on Nov. 14, 2014.

(51) Int. Cl.
*G06Q 50/26* (2024.01)
*G16H 40/67* (2018.01)

(52) U.S. Cl.
CPC .......... *G06Q 50/265* (2013.01); *G16H 40/67* (2018.01)

(58) Field of Classification Search
None
See application file for complete search history.

(56) References Cited

U.S. PATENT DOCUMENTS

| | | | | |
|---|---|---|---|---|
| 5,731,575 | A | 3/1998 | Zingher et al. | |
| 8,260,720 | B1 * | 9/2012 | Dixon | G06Q 40/00 235/382 |
| 8,447,273 | B1 | 5/2013 | Friedlander et al. | |
| 9,672,727 | B1 * | 6/2017 | Alexander | G08B 25/008 |
| 10,387,876 | B1 | 8/2019 | Buentello et al. | |
| 2004/0181483 | A1 * | 9/2004 | Dort | G06Q 20/108 340/5.82 |
| 2008/0251578 | A1 * | 10/2008 | Jansing | G07F 19/20 235/379 |
| 2011/0263946 | A1 * | 10/2011 | el Kaliouby | A61B 5/16 600/300 |
| 2014/0121540 | A1 * | 5/2014 | Raskin | G16H 40/63 600/479 |
| 2014/0347265 | A1 | 11/2014 | Aimone et al. | |
| 2014/0364751 | A1 | 12/2014 | Dugan et al. | |
| 2015/0085872 | A1 | 3/2015 | Palawat et al. | |
| 2015/0093725 | A1 | 4/2015 | Baarman et al. | |
| 2015/0238140 | A1 | 8/2015 | LaBelle et al. | |
| 2015/0269700 | A1 | 9/2015 | Miasnik et al. | |

(Continued)

*Primary Examiner* — Alan Torrico-Lopez
(74) *Attorney, Agent, or Firm* — Plumsea Law Group, LLC

(57) ABSTRACT

A system and method for analyzing wearable sensor data in reconciliation with calendar entry data. A computer processor is coupled to a user configurable calendar system and a user wearable device. The processor detects one or more user activity events from one or more electronic wearable devices associated with the user and detects one or more user calendar events from a user configurable calendar system. The processor is configured to determine a course of action to be taken by the user based upon the one or more calendar events and the detected one or more user events.

20 Claims, 7 Drawing Sheets

(56) References Cited

U.S. PATENT DOCUMENTS

2016/0078430 A1* 3/2016 Douglas ............. G06Q 30/0185
705/43
2016/0086143 A1 3/2016 Hao et al.

* cited by examiner

347

347
346
350
71

345
346
50
41
342
72
71
347
a
b
c
d
e
f
x
y
z 71
351
352

345
341
342
71

SYSTEM, METHOD AND APPARATUS FOR WEARABLE COMPUTING

CROSS REFERENCE TO RELATED APPLICATIONS

This application is a Continuation of U.S. patent application Ser. No. 14/941,234 filed Nov. 14, 2014.

FIELD OF THE INVENTION

The present disclosure relates to the field of wearable technology equipment, and in particular relates to pairing wearable devices with electronic calendar entry systems.

BACKGROUND OF THE INVENTION

The continuous improvements in both software and hardware have led to the development of wearable computing devices. Embodiments of the present invention relate generally to methods and systems for wellness and activity tracking and recommendations and more particularly to integrating wearable devices with electronic calendar entry systems.

Activity Tracking and applications have been gaining a lot of attention recently. The practice of applying data analytics to get quantified feedback and thus change behavior has become widespread over many different regions. This is partly driven by the "Quantified Self" movement which uses technology to collect data from a person's daily life, followed by visualization, cross-referencing, and discovering correlations. This is also driven by the increasing support for the user wellness, which aims to improve the health outcomes of users.

SUMMARY OF THE INVENTION

The purpose and advantages of the below described illustrated embodiments will be set forth in and apparent from the description that follows. Additional advantages of the illustrated embodiments will be realized and attained by the devices, systems and methods particularly pointed out in the written description and claims hereof, as well as from the appended drawings.

To achieve these and other advantages and in accordance with the purpose of the illustrated embodiments, in one aspect, a system and method for analyzing wearable sensor data in reconciliation with calendar entry data is described in which a computer processor is coupled to a user configurable calendar system and a user wearable device. The processor detects one or more user activity events from one or more electronic wearable devices associated with the user and detects one or more user calendar events from a user configurable calendar system. The processor is configured to determine a course of action to be taken by the user based upon the one or more calendar events and the detected one or more user events.

BRIEF DESCRIPTION OF THE DRAWINGS

The accompanying appendices and/or drawings illustrate various non-limiting, example, inventive aspects in accordance with the present disclosure.

DETAILED DESCRIPTION OF CERTAIN EMBODIMENTS

Figure 1:
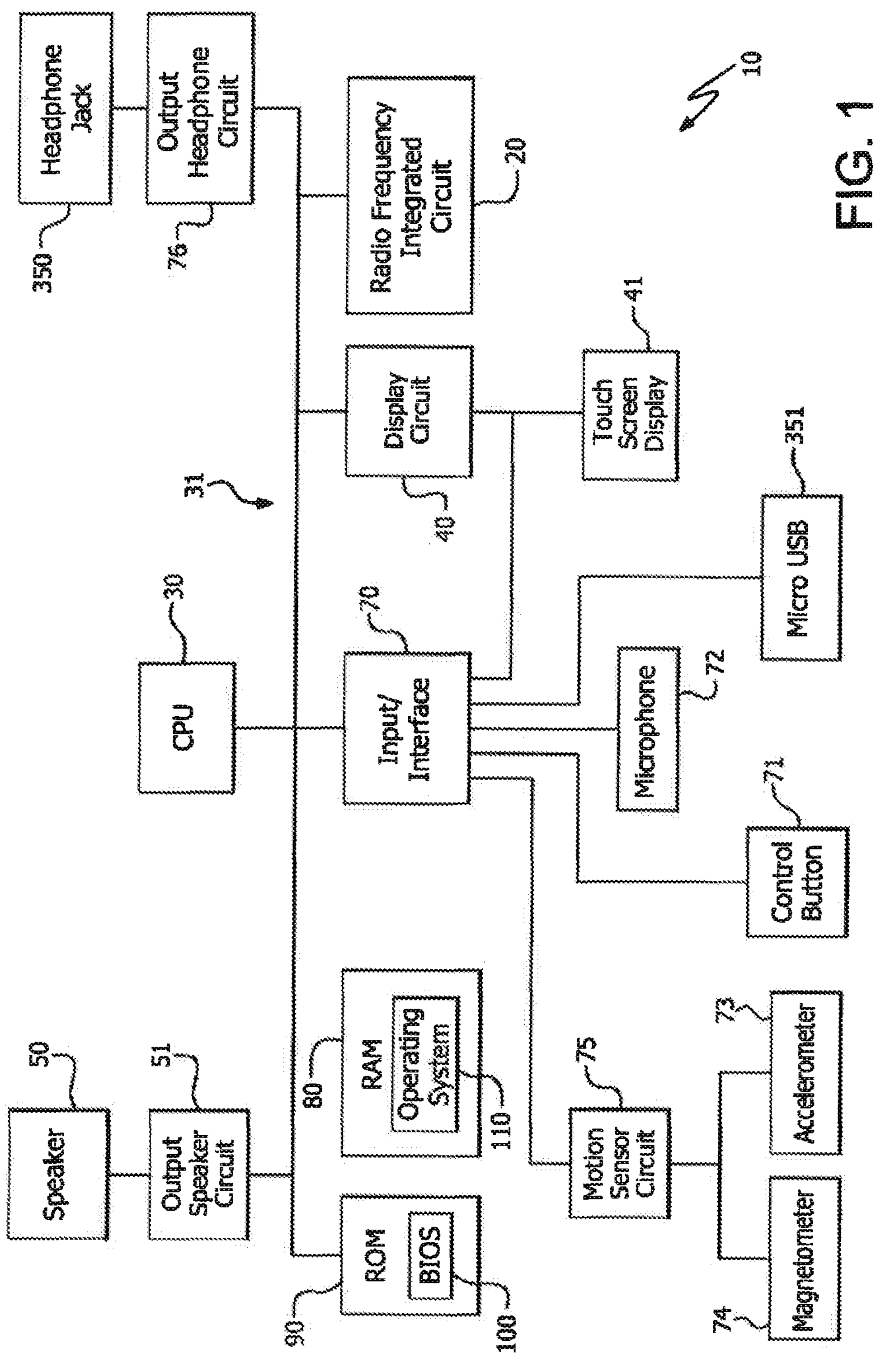
FIG. 1 shows a schematic diagram of one embodiment of a wearable digital media device that may be employed.

Referring to the drawings wherein like or similar references indicate like or similar elements throughout the several views, there is shown in FIG. 1 a schematic diagram of one embodiment of a wearable digital media device that may be employed, generally identified by reference numeral 10. Central Processing Unit 30 ("CPU") operates as the main control unit for the personal digital media device. The CPU 30 can be any microprocessor that is capable of being programmed to perform the various functions required by the personal digital media device. In a preferred embodiment, CPU 30 is a microcontroller unit with integrated RAM, ROM and input/output code and circuitry configured to perform the functions herein described. CPU 30 is programmed with the driver software necessary to control and enable each of the circuits connected to CPU 30. In addition, CPU 30 is programmed with application software to allow the user to perform functions on the database stored in the device. CPU 30 is electrically connected to and controls the other circuits in the wearable digital media device via bus 31.

Output headphone circuit 76 is electronically connected to CPU 30. Output headphone circuit controls headphone jack 350 and permits connected headphones (not depicted) to receive audio output content.

Display circuit 40 is electrically connected to CPU 30. The display circuit 40 controls the touch screen display 41 used to provide information to the wearable digital media device user. The touch screen display 41 can display graphical content and also incorporates an SRS touch panel for receiving input from a user. Speaker 50 is electrically connected to CPU 30 via output speaker circuit 51. Speaker 50 creates an audible sound according to one embodiment of this invention, as further explained herein. Input interface circuit 70 is electrically connected to CPU 30, microphone 72, control button 71, display screen 41, and motion sensor circuit 75, which comprises magnetometer 74 and accelerometer 73. The input interface circuit 70 receives data input from the wearable digital media device user though microphone 72, control button 71, display screen 41, motion sensor circuit 75, magnetometer 74, micro USB 351, and/or accelerometer 73 and, in turn, conveys certain data input to CPU 30. In other embodiments, there are more than one control button 71 (not depicted). In another embodiment, input interface 70 can receive sound information, such as a digital media device user's voice, through a microphone 72.

Radio frequency integrated circuit 20 is electrically connected to CPU 30. The radio frequency integrated circuit 20 facilitates wireless communication between the wearable digital media device and another device, such as a personal computer, tablet computer, smart phone, or other host processing device, with its own radio frequency integrated circuit, each adapted to send and receive radio frequency transmissions from one another. The radio frequency integrated circuit 20 can be utilized to send and receive data, including, for example, data corresponding to a serial identification number unique to the wearable digital media device. In a preferred embodiment, the radio frequency integrated circuit 20 is of the type typically used by those having ordinary skill in the art for the purposes described herein, including: (1) an integrated CMOS RF receiver, combined with a dual 64-byte buffered framer block; (2) a self-contained, frequency-hopping FSK data modem, optimized for use in the widely available 2.4 GHz ISM band; and (3) contains a frequency synthesizer, a power amplifier, a 12 MHz crystal oscillator, a demodulator, a modulator and an auto-Ack protocol engine; however, other radio frequency technology known to those having ordinary skill in the art, such as Bluetooth or Wi-Fi may be utilized as well.

The wearable digital media device incorporates mass memory. The mass memory includes RAM 80 and ROM 90. In one embodiment, ROM 90 is flash memory that includes content BIOS, operating system program, and application programs stored in memory. RAM 80 is used for run time memory. In a preferred embodiment, the wearable digital media device incorporates mass memory in CPU 30. In one embodiment, hard disk drives and other more permanent storage devices are not utilized since those devices would increase the cost of the wearable digital media device and such storage within the wearable digital media device is otherwise unnecessary in view of the instant invention's utilization of a personal computer or other host processing device (such as a smart phone or other device programmed and configured to perform the functions of a personal computer herein described) to store certain information, as further explained herein. In one embodiment, RAM 80 is sufficient to store operating system 110 to control the operation of the personal digital media device. Any general-purpose operating system may be employed with a basic input/output system ("BIOS") 100 for controlling the low-level operation of the personal digital media device. In one embodiment, operating system 110 and BIOS 100 is incorporated into CPU 30.

In other embodiments, the mass memory described above may incorporate computer-readable media, such as computer storage media commonly recognized by those having ordinary skill in the art, such as flash memory or any other medium which can be used to store the described information and can be accessed by the personal digital media device. The mass memory stores program code and data. Applications are loaded into the mass memory and run on operating system 110. Such applications may include user interface programs interfacing with database programs and the like. The mass memory is further configured to store information related to a serial identification number unique to the personal digital media device.

In one embodiment of the present invention, application software may include a graphical user interface prompting the wearable digital media device user to complete the missing letters of a partially spelled word. In another embodiment of the present invention, application software may include a graphical user interface prompting the wearable digital media device user to supply the sum, product, quotient, missing value, or other input in response to a mathematical question. The wearable digital media device user's input will be stored in the personal digital media device's mass memory within a database for subsequent use and access in accord with the invention further described herein. In another embodiment of the present invention, application software may include a graphical user interface prompting the wearable digital media device user to supply one of a series of possible displayed selections. This may be commonly recognized as a multiple-choice question. In the case of the spelling, mathematical, general knowledge, logical operations, or multiple-choice application embodiments herein described, the wearable digital media device user's selections can be stored in the mass memory of the wearable digital media device and/or sent via radio frequency to another device, such as a personal computer or other host processing device. Additionally, the other device, such as a personal computer, may utilize radio frequency transmissions to send subsequent application questions or other content to the wearable digital media device user through the use of digital signals. In a preferred embodiment, the connection between the wearable digital media device and the other device can be utilized along with application software on the other device programmed and configured to: (i) prepare reports summarizing a digital media device user's mastery of the learning content which may be, for example, sent to a parent via e-mail or accessed on the host processing device or through any browser connected device, such as another personal computer (other than the host processing device), a tablet personal computer, or a smart phone; (ii) permit a supervisor, such as a teacher or parent, to use the other device to monitor the wearable digital media device user's progress through the learning content at any time; (iii) send text or audio messages from the other device to the personal digital media device; (iv) adjust the wearable digital media device settings using the other device; and (v) add, delete or modify the learning content sent from the other device to the personal digital media device.

Figure 2:
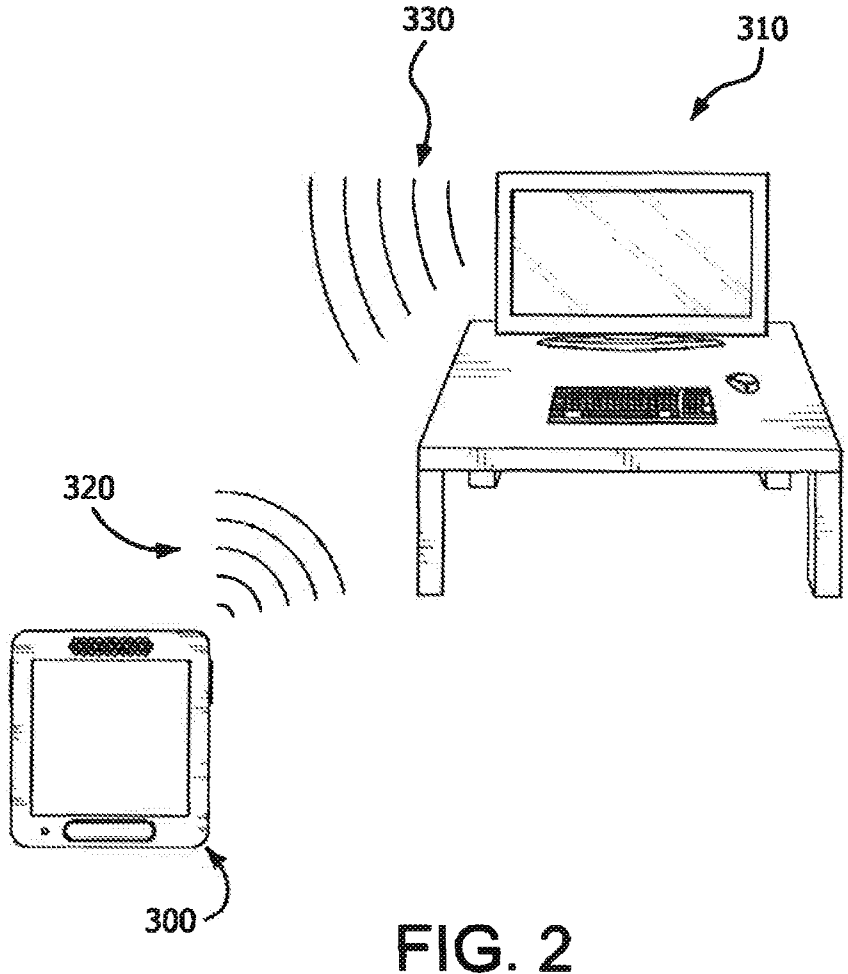
FIG. 2 shows a functional diagram illustrating an environment for practicing the invention.

FIG. 2 shows a functional block diagram illustrating an environment for practicing the invention via a system for communication by and among a personal computer 310 and a wearable digital media device 300 according to one embodiment of the instant invention. While this embodiment exemplifies the use of a personal computer, any host processing device, such as a smart phone or other device programmed and configured to perform the functions herein ascribed to a personal computer, can be utilized. In this embodiment of the instant invention, a personal computer 310 is configured to perform actions which include the use of a radio frequency integrated circuit that is configured to send and receive content through the use of digital signals with a wearable digital media device 300, as shown by radio frequency transmission 330. Personal computer 310 contains a database file and file system within its mass storage to store and recognize a unique serial identification number corresponding to a wearable digital media device 300 where the unique serial identification number is transmitted by the wearable digital media device 300 by radio frequency transmission of digital signals, as shown by radio frequency transmission 320. The wearable digital media device 300 is also configured with a radio frequency integrated circuit (also referred to as a transmission signal module) that is configured to send and receive content with the personal computer 310 in the form of digital signals. The wearable digital media device 300 is programmed with a unique serial identification number.

Figures 3, 4, 5, 6, 7:
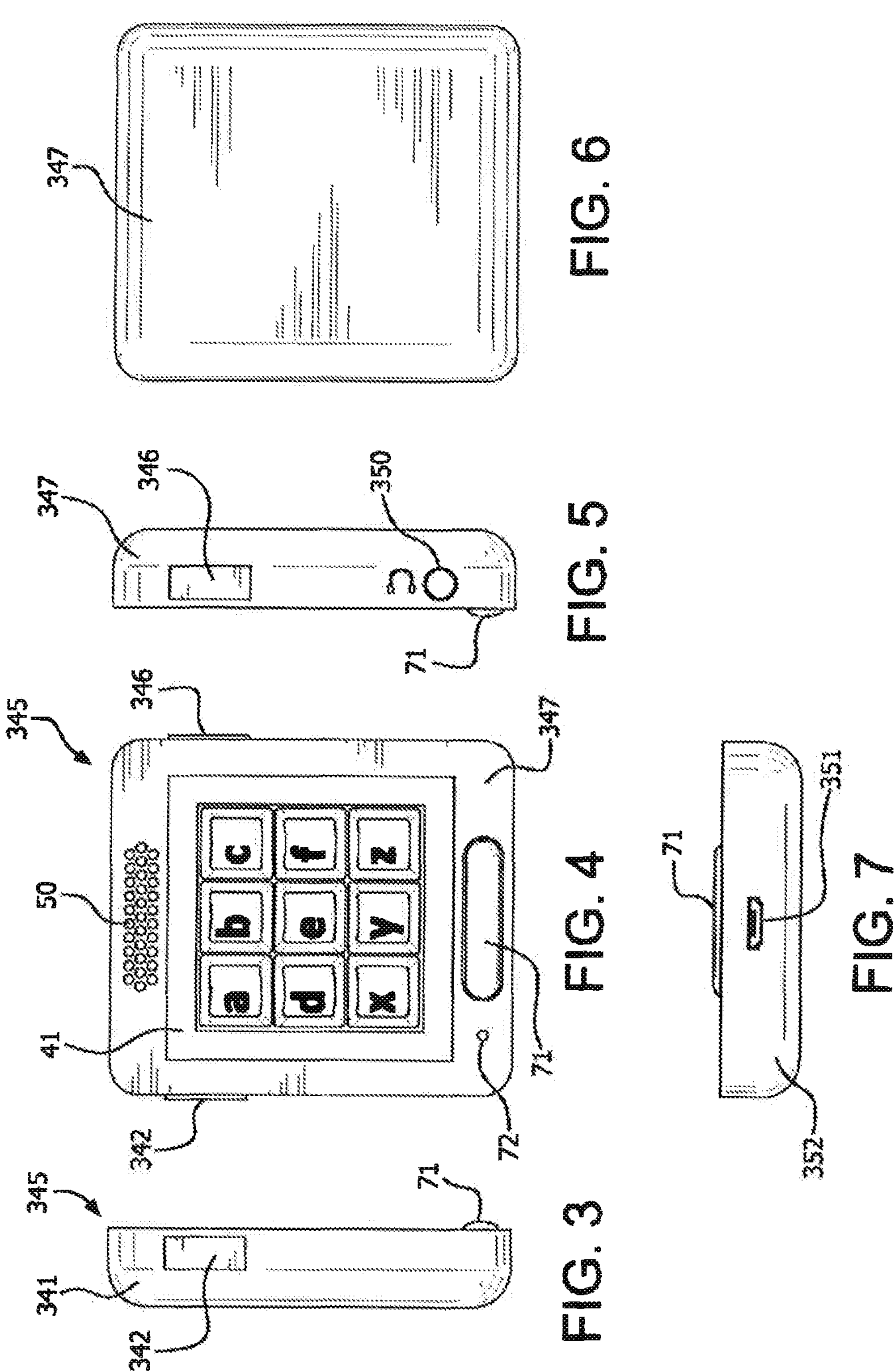
FIG. 3 shows a perspective view of one embodiment of the wearable digital media device.
FIG. 4 shows a perspective view of one embodiment of the wearable digital media device.
FIG. 5 shows a perspective view of one embodiment of the wearable digital media device.
FIG. 6 shows a perspective view of one embodiment of the wearable digital media device.
FIG. 7 shows a perspective view of one embodiment of the wearable digital media device.

FIGS. 3 through 7 exemplify one embodiment of the instant invention. In FIG. 3, the wearable digital media device is generally identified by reference numeral 345. Wearable digital media device 345 is depicted in FIG. 3 from the left side 341. Left side 341 has first custom button 342. In FIG. 4, wearable digital media device 345 is depicted from the front side, facing screen 41. FIG. 4 depicts front side 347 with speaker 50, control button 71, microphone 72, first custom button 342 and second custom button 346. Both first custom button 342 and second custom button 346 are additional input mechanisms that are, in this embodiment, electronically connected to the input interface 70 depicted in FIG. 1 (not depicted). FIG. 5 depicts right side 347 with headphone jack 350. FIG. 6 depicts rear side 348. FIG. 7 depicts bottom side 352, showing Micro USB Port Connection 351 and control button 71.

Figures 8, 9, 10:
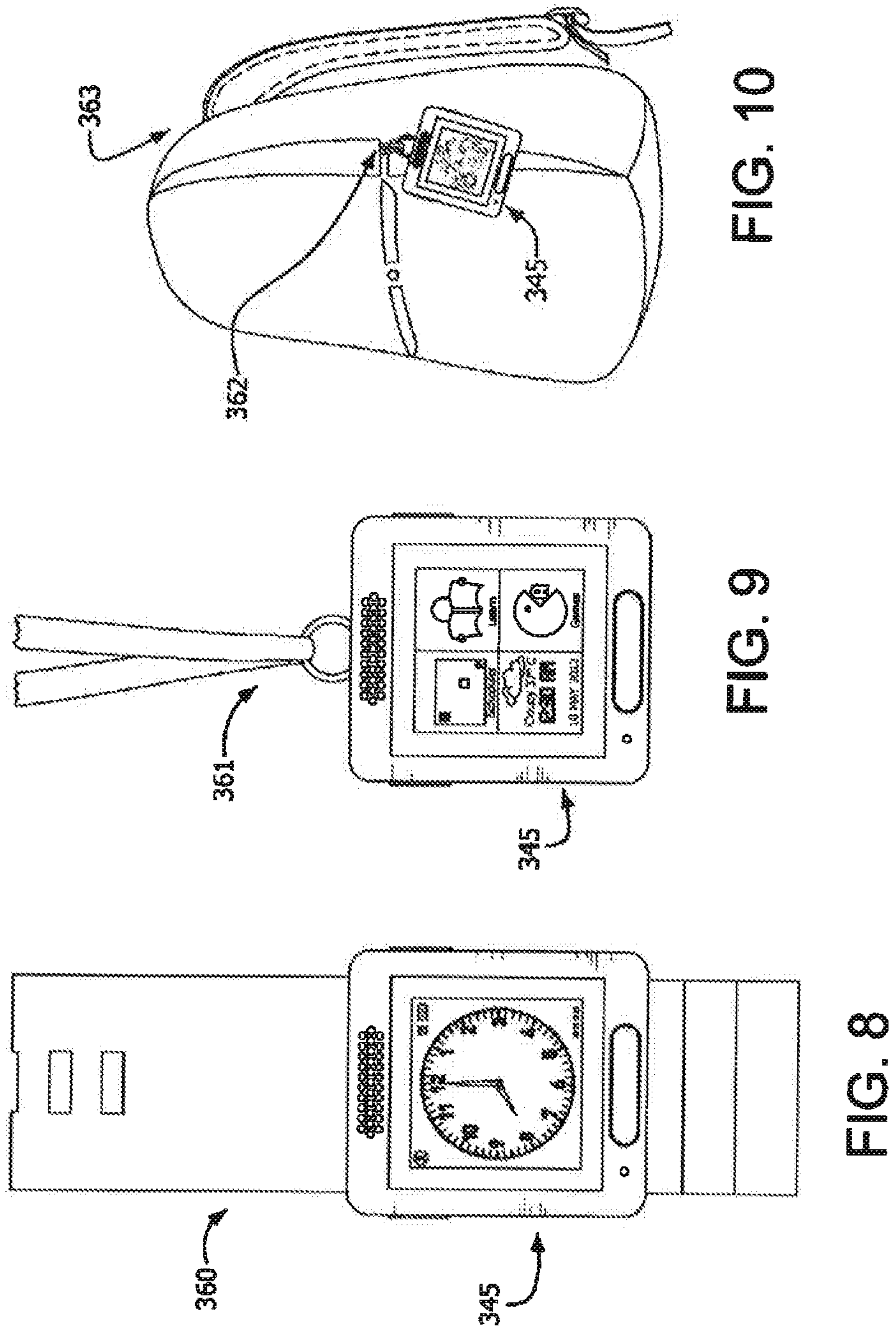
FIG. 8 shows a perspective view of one embodiment of the wearable digital media device.
FIG. 9 shows a perspective view of one embodiment of the wearable digital media device.
FIG. 10 shows a perspective view of one embodiment of the wearable digital media device.

FIGS. 8 through 10 depict wearable digital media device 345 connected to various attached articles by way of an attaching fastener. In FIG. 8, wearable digital media device 345 is attached to a watch 360. In FIG. 9, wearable digital media device 345 is attached to pendant 361. In FIG. 10, wearable digital media device 345 is attached to keychain 362. Keychain 362 is attached to book bag 363.

Figure 11:
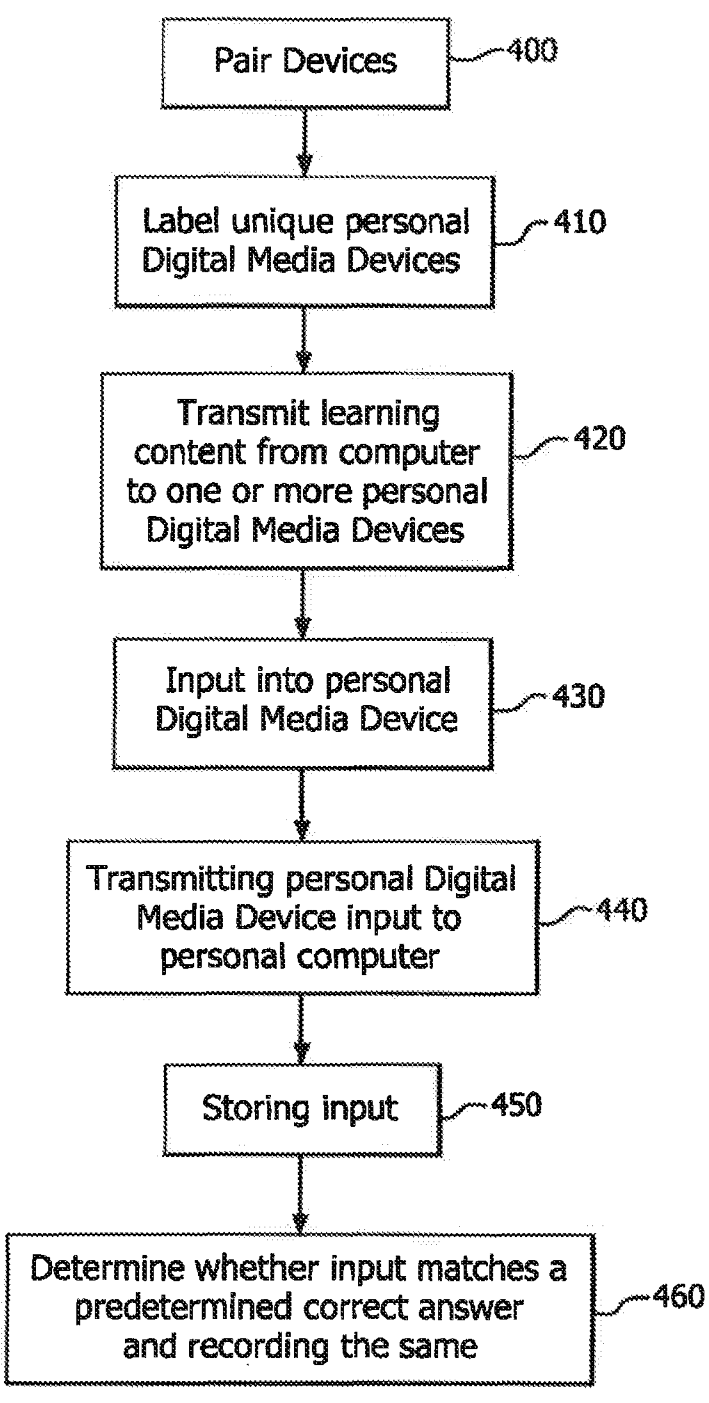
FIG. 11 is flow chart illustrating a method for carrying out one embodiment of the invention.

FIG. 11 is flow chart illustrating one embodiment of a system for carrying out one embodiment of the invention. According to this embodiment of the instant invention, a wearable digital media device and a personal computer are paired in step 400 by sending and receiving content with radio frequency integrated circuits incorporated in the wearable digital media device and a personal computer. The content is transmitted in the form of digital signals. While this embodiment exemplifies the use of a personal computer, any host processing device, such as a smart phone or other device programmed and configured to perform the functions herein ascribed to a personal computer can be utilized. The paring step 400 is completed after a processor in the personal computer is adapted to recognize the unique serial number associated with the personal digital media device. Accordingly, a plurality of personal digital media devices, each with their own unique serial number, can be independently paired with a personal computer.

Once the devices are paired, the personal computer user can label the paired wearable digital media device (or devices) with a user-selected name in step 410. A personal computer user may, for example, desire to designate a user-selected name as a way to identify which wearable digital media device may correspond to which wearable digital media device user. By way of a more specific example, a parent with two children using personal digital media devices may label each device in step 410 with the name of the child utilizing each respective device. In an alternative embodiment, step 410 is not utilized.

Figure 12:
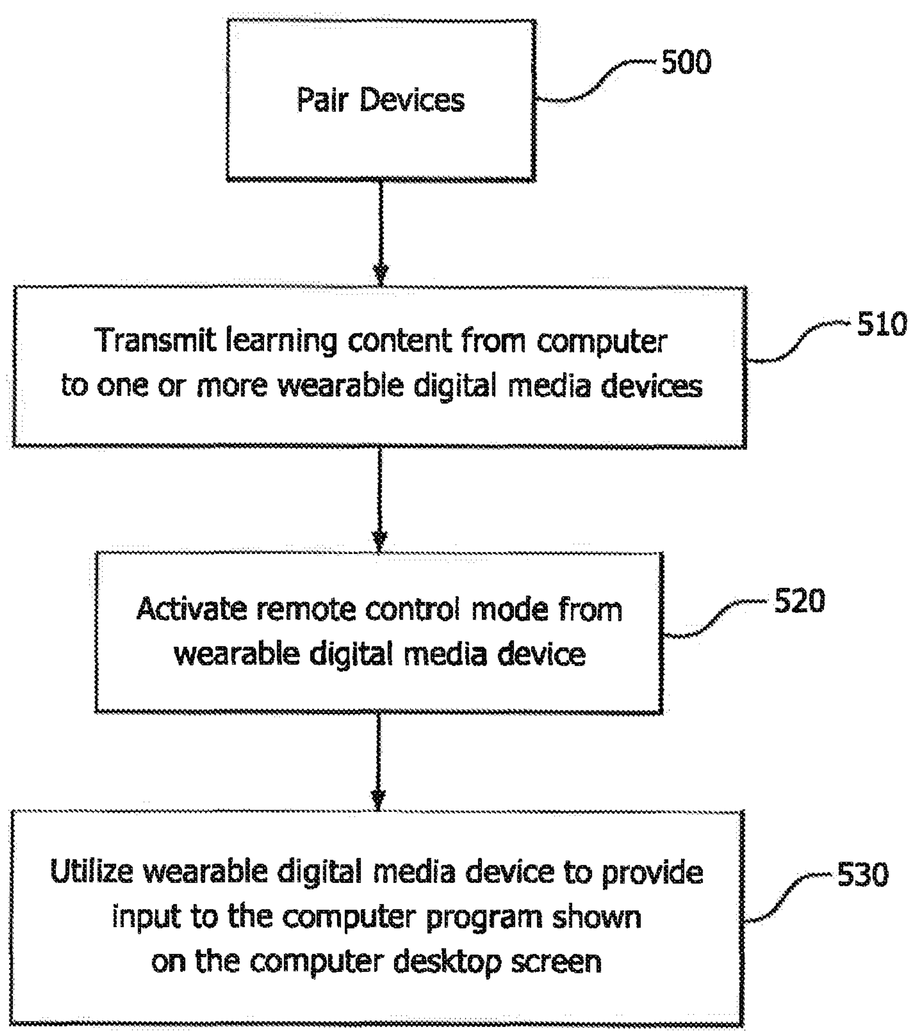
FIG. 12 is flow chart illustrating a method for carrying out another embodiment of the invention.

Content, such as learning applications with spelling questions, mathematical questions, general knowledge questions or logical operations questions, as well as other data, including, scheduling data, voice messages and text messages, are transmitted in the form of digital signals from a personal computer to each paired wearable digital media device with radio frequency integrated circuits incorporated in each paired wearable digital media device and the personal computer at step 420. This connection is illustrated by FIG. 12. At step 500, the wearable digital media device is paired to a computer, which may be a personal computer, smart phone or tablet computer, for example. At step 510, content, such as learning applications, is transmitted from the computer to one or more wearable digital media devices. At step 520, the remote control mode can be activated from the menu of the wearable digital media device. At step 530, a user may utilize the wearable digital media device to provide input to the computer program shown on the computer desktop screen.

Returning to FIG. 11, in step 430, the paired wearable digital media device user is provided with content, such as learning applications, displayed on the paired wearable digital media device screen and/or broadcast through the personal digital media device's speaker and the wearable digital media device user is prompted to input a response to the learning content.

In an alternative embodiment, the content, such as learning applications, is displayed on the screen of a paired personal computer, tablet computer, or smart phone using the means of data sharing herein disclosed. In this alternative embodiment, the wearable digital media device content can be displayed on, typically, a larger screen. As a consequence of this alternative embodiment, a user can operate the wearable digital media device and simultaneously view the content on the wearable digital media device touch screen display on the screen of another paired device.

In step 440, the paired wearable digital media device user's input in response to content, such as learning applications, is transmitted as digital signals to a paired personal computer via radio frequency integrated circuits incorporated in the paired wearable digital media device and the computer.

At step 450, the paired wearable digital media device user's input is stored in a database file and file system within the mass memory of the wearable digital media storage device. Additionally, or in the alternative, the digital media device user's input is stored in a database file and file system within the mass memory of the personal computer. In a preferred embodiment, the said input is stored exclusively on the wearable digital media storage device mass memory in order to operate the wearable digital media device independently of a host computer.

At step 460, a programmed personal computer and a processor adapted to the programmed personal computer's memory is used to compare the stored wearable digital media device user's input to a pre-determined correct input pursuant to a programmed application and storing information with respect to whether or not the user's input matches the correct input for the respective prompt in a database file and file system. In a preferred embodiment, step 460 is performed by the wearable digital media device, independently of the programmed personal computer.

By way of example, an application operating on a personal computer (or, in the preferred embodiment, the wearable digital media device) can contain learning content, such as a bank of questions appropriate to spelling, mathematical or other subjects. The question bank can be categorized by increasing levels of complexity. Questions can be sent according to the method herein described in step 420 from the personal computer to the personal digital media device (or, in a preferred embodiment, the questions already reside within the memory of the wearable digital media device and are merely recalled by the operating system). The wearable digital media device user can respond to the transmitted spelling question, math question or multiple choice question, for example, in step 430. The wearable digital media device user's input response can be transmitted back to the personal computer in step 440 through the use of a digital signal and then stored in the mass memory of the personal computer in step 450 (though, in other embodiments, it may also be optionally stored in the personal digital media device's mass memory). Based on the comparison performed in step 460, a wearable digital media device user's response would be recorded in the personal computer's mass memory as either correct or incorrect (or, in the preferred embodiment, the recording would be made within the mass memory of the wearable digital media device). If the response is incorrect, the question can be flagged in the personal computer's mass memory (or, in the preferred embodiment, the question is flagged in the wearable digital media device's mass memory and optionally sent to the personal computer's mass memory with the process herein described). A parent operating the personal computer, for example, can see which questions the student has supplied correct answers for and which questions were incorrect. Questions with incorrect answers can be transmitted to the wearable digital media device user for one or more subsequent attempts. In other embodiments, the application software will iterate to increasingly difficult categories of questions based on the student's mastery of less difficult material. In other embodiments, questions are not categorized, but instead offered at random or by some other ordering.

By way of a further example, the system herein described can be utilized by a teacher in a classroom environment. Each student can utilize his or her own personal digital media device. The teacher may quiz students by inputting pre-determined or teacher-created questions into a personal computer which can be sent to the students according to the system described herein and depicted in FIG. 3. Alternatively, according to another embodiment, students may send a signal using the personal digital media device, which would be received at a teacher's personal computer in a manner that utilizes the device labels herein described in order to identify which of a plurality of wearable digital media device users sent the said signal as an alternative to the student raising his or her hand to attract the teacher's attention.

In another embodiment, the digital signal transmitted to the wearable digital media device from a personal computer can signal a command to broadcast an audible sound (also referred to as an audible signal) from a speaker by way of a processor in the wearable digital media device being further adapted to receive such data and broadcast such sound. In yet another embodiment, the speaker is used to broadcast the audible form of the learning content transmitted to the wearable digital media device in addition to or as an alternative to displaying the learning content on the wearable digital media device screen.

In yet other embodiments, and in conjunction with, the above disclosed illustrated embodiments, further illustrative embodiments include what is described below.

Smart Phones are typically "worn" by users in that they are often carried in clothing or in close proximity to the person. Sensors attached to the person, may be integrated into clothing or in the fabric itself, or part of a button or other clip-on device on the member's clothing. The sensor that is attached with (adhesive tape behind the ear, with an elastic band under member clothing as with exercise heart rate monitors) could include optical, sound, biometric, GPS, heat, acceleration, radiation or other sensing capabilities. Smart phone may cooperate with other worn sensors and act as a communication gateway to USAA of simple sensing data from other sensors worn by member. Wearable sensor(s) on member could communicate with smart home or smart vehicle devices to relay data from wearable computing device(s) to USAA or to the home or vehicle.

One-way information from wearable devices to USAA to establish profile on member, or on group of people associated with member (e.g. family). USAA could gather and process over time more detailed information that is compiled and used to provide better future offers of services or savings to user. USAA could aggregate data for the member family group that improves the relevance of offers to member and member family. One-way information may be shared with other entities on an opt-in basis by the member, such as to vendor at which member is currently shopping. Two-way communication between member and USAA where certain data monitored by USAA and warnings or advice based on the data transmitted back to one or more of the wearable computing devices of the member.

Wearable computing devices may provide heart rate warning providing complex advice to member on closest hospital and directions to ER. Sensor could produce sound, vibration, electrical impulse or etc. detectable by the member wearing the sensor. Sensor(s) could be intelligent enough to only transmit data to server if a certain pattern of data is detected so that power and bandwidth is minimized Wearable Computing Devices may include biometric tracking Applications whereby wearable device(s) could be used to track information such as heart rate, respiration rate, limb movement and orientation and/or temperature for member. USAA could use this data in a real-time fashion to augment authentication procedures that identify the user in high value transactions based on historical readings for member (patterns of user biometric data over time stored and checked against current situation). Detect danger or duress of member (hold-up situation at ATM) and use data to automatically adjust surroundings (alter ATM behavior to display false balance data, limit withdrawal amount available, etc.) and call for help. Danger may be indicated by a predetermined action/signal agreed on by the member or by a break from a known pattern of action. Detect medical distress (heart attack, atrial fibrillation, fever) and call for medical assistance, arrange for future appointments and order medication. Monitor vital signs over an extended period and adjust health insurance rates automatically after testing period (improve rates from base rate, or simply offer a better base rate for just participating in wearable computing monitoring). Track biometrics and provide real-time feedback to member on complex sensor tracking. Hydration example where sensors tracking respiration, heart rate, temperature and (lack of) sensed movement of hand toward mouth could be processed to determine that the member needs to hydrate. Member could be informed, directed to vendor and made offer of beverage discount.

Detect danger to member (hold-up situation at ATM) and use data to automatically adjust surroundings (display false data on ATM, limit withdrawal amount) and call for help. Could track member in conjunction with smart home/vehicle sensors and warn to move to certain room or door based on sensed problems and dangers in the local environment.

Wearable computing devices may be configured and operational to improve user physical performance—e.g., notify that running stride too long, and thus needs to be shortened, as determined by analytics of user performance and body type/dimensions. Determine user patterns and habits and adjust to preferences determined from patterns.

Wearable computing devices may be configured and operational to predict future events (e.g., wearing certain "smart" pants will trigger certain events (user is going to work-shut house down, auto start car (check fuel level), check traffic routes to work, etc.)). Provide catastrophe assistance program, where after/during an accident or disaster USAA may work with emergency service providers to track whereabouts of members and/or provide some useful data on types of injuries. Provide indication of last known location. Provide current heart rate and temperature. Accelerometer data in clothing could detect breathing. Recent accelerometer data from wearable clothing that might hint at broken bones or concussions. Automate hospital triage. Provide emergency beacon or child-tracking whereby wearable device(s) automatically activate locator beacon function upon detection of certain events—wearable devices automatically initiate beacon function in response to server inquiry.

Wearable computing devices may be configured and operational to provide pre-existing condition monitoring intelligent enough to recognize that certain elevated readings are not an emergency event—e.g. heart condition known, but also known and detected that member has a history of higher heart rate when eating spicy foods in the early afternoon at restaurants in a certain location such that an alert would be avoided based on prior experience. Determine user location to provide a real-time geography risk profile/assessment (e.g., college student leaving geo-fence at a certain time indicates unusual activities). Focus on children and elderly.

Wearable computing devices may be configured and operational to provide life coach applications whereby wearable computing devices may gather data on all aspects of a member's life including shopping, fitness activities, travel, sleep habits, safety habits (e.g. using a seatbelt), health and eating and etc. and comment to member on these features.

Wearable computing devices may be configured and operational to provide a "Tour guide mode" whereby USAA can use the data to sense where the user is and what the user is seeing so that descriptions of the surroundings can be provided and the member educated on his/her situation and location (e.g., combine with Google glasses as one of the wearable computing devices).

Wearable computing devices may be configured and operational to link wearable computing data to member calendar and advise on best course of action, sense location and eating activity and advise not to eat too much due to big dinner planned that evening, advise to carbo load at mealtimes prior to big race. Sense clothing selections (sensors in clothes) based on calendar events—type of clothes, clothing taste sensor (no green plaid pants with pink velvet shirt for formal dinner)—and notify if changes needed. Link wearable computing data to member calendar and advise on best course of action. Provide budgets and recommendations while member is shopping (based on shopping lists, life event issues and other info USAA tracks). Determine user patterns and habits (e.g., wearing certain "smart" pants will trigger certain events (user is going to work—shut house down, auto start car (check fuel level), check traffic routes to work, etc.)).

Wearable computing devices may be configured and operational to provide shopping and marketing related services. Provide store finder, or in-store guidance, transmitted to member. Provide advice to member based on past tracked buying habits, current location, possibly linked to present budget status and type of store or product that would satisfy product need and budget. Tie into vendor computing devices, GPS locations, member shopping lists and budgets. Addiction/health improvement module that routes member away from the liquor store/aisle, candy store/aisle or whatever other vice the member may have been struggling with. Indirect marketing module that routes member by (on road or in store) products or stores without specifically calling them out—as a way to let third parties subtly advertise through USAA to member without member feeling they are being bombarded by direct advertising and offers. Provide a "Privacy Shield" protection of member data and outputs from wearable computing—camouflages member identity and wearable computing output information from prying vendors while enabling members to shop somewhat anonymously and keeps others from sniffing user sensor data. May be an interfering/jamming signal or one that sends false information (i.e. transmitting misinformation, such as a phony profile that does not appear fake on its face, rather than making member invisible). Could be a manual or automatic feature that allows USAA members to say "enough" to previously permitted data sharing and to illicit data snooping.

Wearable computing devices may be configured and operational to provide insurance policy recommendations based on physical condition, or travel location data. Provide pattern of location information may indicate type of travel or vehicle insurance needed. Steep changes in elevation and/or pressure could indicate scuba diving, flying, sky-diving and etc.

Wearable computing devices may be configured and operational to allow USAA members use body heat or motion to charge the wearable computing devices and integrate a wearable device (including smart phone) charger into health club or home gym equipment for green footprint.

Figure 13:
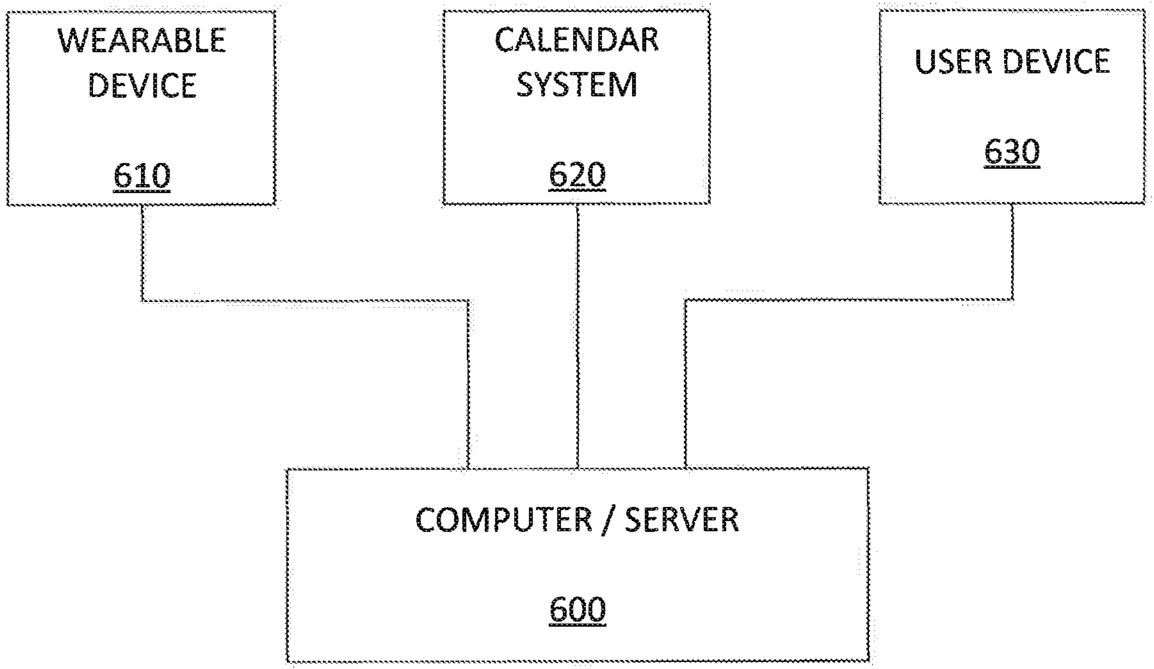
FIG. 13 shows a schematic diagram of another embodiment of a wearable system that may be employed.

For instance, and with reference now to FIG. 13, yet another illustrative embodiment is now described. As to be now discussed, a computing device 600, such a computer/server (which may reside in the cloud) is preferably linked to an electronic calendar system 620 having user calendar entries indicating planned user activity and locations to be visited by a user preferably during a prescribed time period. Examples of such an electronic calendar include (but are not limited to): MICROSOFT OUTLOOK™; APPLE ICAL™ AND GOOGLE Calendar™. A network adapter preferably links the computing device 600 to such an electronic calendar, which is preferably cloud based. Such a calendar 620 may also locally reside on a user electronic device 630 which couples to computing device 600 via a host of known interfacing techniques.

The computing device 600 also links (preferably via a network adapter) to a plurality of computing wearable devices 610 as described herein. Examples of such wearable devices 610 include (and are not limited to) wearables having GPS functionality to track user locations (e.g., a smartwatch device and/or a smart phone device) and wearables configured to monitor/detect a health condition of a user, including heart rate, blood sugar level, hydration level, futility, stress and the like. The computing device 600 also preferably links (preferably via a network adapter) to one or more user computing devices 630 capable of interacting with computing device 600 so as to provide notices/information to a user in accordance with the teachings herein. Examples of such user computing devices 630 include (and are not limited to), desktop/laptop computers, smart phone devices, tablet devices, interactive televisions and other similar consumer computing devices.

In use, and with the computing device 600 coupled to a user configurable calendar system 620, the computing device 600 detects one or more user activity events from the one or more electronic wearable devices 610 associated with the user. Examples of such events include, and are not limited to: a user's location; mode of travel (walking, biking, automobile, plane, train, running, etc), a health condition of a user (including heart rate, blood sugar level, hydration level, futility, stress and the like), type of clothing a user is wearing, a user's perspiration activity level and/or composition, a user's weight and the like. The computing device 600 also is configured to detect one or more user calendar events from the user configurable calendar system 620. Examples of such user calendar events include, and are not limited to: a user's work schedule, travel schedule, vacation schedule, entertainment events (such as meal events (e.g., breakfast, lunch, dinner, drinks, etc.), theater, and the like, activity events (such as hiking, running, biking, swimming and the like), appointments (such as Dr. appointments, car repair, home repair, and all other types of appointments), family planning, and any other type of event suitable for a calendar entry.

Once the computing device 600 has captured the aforesaid user activity events (via wearable devices 610) and the user calendar events (via calendar 620), the computing device 600 is configured to determine a course of action to be taken by the user based upon the one or more calendar events and the detected one or more user events. Notification of this course of recommended action is preferably provide to the user via a user device 630. It is to be appreciated a determination is made as to whether the detected one or more calendar events has relevance to the detected one or more user events for a prescribed time period. For instance, if a calendar event indicates a user is to consume a large meal at 7 μm and the wearable device 610 indicates a user is at a location serving food within three hours from 7 μm, the system 600 may remind the user not to consume too much food, or may even suggest what items to consume based upon the user's location (computer system 600 determines the food service vendor the user is present at based on the user's location). Similarly, the system 600 may determine the user needs to depart a certain location (based upon the user's current location) to arrive on time for a calendar event having a specified location and time. A calendar event may indicate the user is to participate in an upcoming activity event (e.g., a marathon race) and the wearable device 610 may indicate a current user health activity that may be detrimental to the upcoming activity event (e.g., excess heart, low blood sugar level, and/or high stress) whereby the system 600 provides notification to the user indicating the user should curb/modify their existing health condition so as to be better prepared for the aforesaid upcoming activity event.

Although the invention has been described with reference to specific embodiments, this description is not meant to be construed in a limited sense. Various modifications of the disclosed embodiments, as well as alternative embodiments of the invention, will become apparent to persons skilled in the art upon reference to the description of the invention. It is, therefore, contemplated that the appended claims will cover such modifications that fall within the scope of the invention.

What is claimed is:

1. A system for analyzing wearable sensor data to affect changes to a device a user is interacting with, comprising:

a personal digital media device on the person of a user and coupled to one or more electronic wearable devices associated with the user wherein the personal digital media device includes a memory and a processor disposed in communication with the memory and configured to issue a plurality of instructions stored in the memory such that the processor:

detects a user duress health condition from the one or more electronic wearable devices associated with the user using one or more biometric sensors by comparing present readings detected by the one or more biometric sensors with historical readings for the user;

detects danger to the user as determined by a break from a known pattern of action;

determines, responsive to detecting the user duress health condition and danger to the user, a device the user is interacting with using information received from the one or more electronic wearable devices associated with the user;

augments an authentication procedure associated with the device the user is interacting with; and transmits, responsive to detecting the user duress health condition and danger to the user and determining the device the user is interacting with, an electronic signal to the determined device the user is interacting with to change performance of the device the user is interacting with.

2. The system as recited in claim 1, wherein the device the user is interacting with is an Automated Teller Machine (ATM).

3. The system as recited in claim 2, wherein the change in performance of the ATM causes the ATM to display false balance data.

4. The system as recited in claim 2, wherein the change in performance of the ATM causes a limit in a withdrawal amount available.

5. The system as recited in claim 2, wherein the change in performance of the device causes communication with a first responder.

6. The system as recited in claim 1, wherein the processor is further instructed to send a signal to a third party indicating the user is under a health condition while interacting with the device.

7. The system as recited in claim 1, wherein the one or more electronic wearable devices includes a health monitoring device.

8. The system as recited in claim 7, wherein the one or more health conditions include user heart rate.

9. The system as recited in claim 8, wherein the one or more health conditions further includes user stress level.

10. The system as recited in claim 7, wherein the one or more health conditions include a blood sugar level associated with the user.

11. The system as recited in claim 7, wherein the transmitted electronic signal consists of a radio frequency electronic signal.

12. A computer-implemented method for analyzing wearable sensor data, comprising:

detecting, in a computer processor of a personal digital media device on the person of a user, a user duress health condition from one or more electronic wearable devices associated with the user using one or more biometric sensors by comparing present readings detected by the one or more biometric sensors with historical readings for the user;

detecting danger to the user by determining a break from a known pattern of action;

detecting, in the computer processor, a user location from GPS information received from the one or more electronic wearable devices associated with the user and a location of an Automated Teller Machine (ATM) responsive to detection of user duress and danger to the user;

augmenting an authentication procedure associated with the ATM; and transmitting, via a communication network, from the computer processor, responsive to the detected danger to the user and detected user duress health condition from the one or more electronic wearable devices, a radio frequency electronic signal to the detected ATM the user is interacting with to change performance of the ATM.

13. The computer-implemented method as recited in claim 12, wherein the change in performance of the ATM causes the ATM to display false balance data.

14. The computer-implemented method as recited in claim 12, wherein the change in performance of the ATM causes a limit in a withdrawal amount available.

15. The computer-implemented method as recited in claim 12, wherein the change in performance of the ATM causes communication with a first responder.

16. The computer-implemented method as recited in claim 12, wherein the computer processor is further instructed to send signal to a third party indicating the user is under duress while interacting with the ATM.

17. The computer-implemented method as recited in claim 12, wherein the one or more electronic wearable devices includes a health monitoring device.

18. The computer-implemented method as recited in claim 17, wherein the one or more health conditions include user heart rate.

19. The computer-implemented method as recited in claim 18, wherein the one or more health conditions further includes user stress level.

20. The computer-implemented method as recited in claim 17, wherein the one or more health conditions include a blood sugar level associated with the user.

* * * * *